(12) United States Patent
Naniki et al.

(10) Patent No.: US 11,247,961 B2
(45) Date of Patent: Feb. 15, 2022

(54) METHOD FOR REMOVING OR COLLECTING 2-ALKOXYETHANOL, AND METHOD FOR PRODUCING (2-ALKOXYETHYL) VINYL ETHER

(71) Applicant: MARUZEN PETROCHEMICAL CO., LTD., Chuo-ku (JP)

(72) Inventors: Takashi Naniki, Ichihara (JP); Ryuichi Tenjimbayashi, Ichihara (JP); Masuo Yamazaki, Ichihara (JP); Tomohiko Sato, Chuo-ku (JP)

(73) Assignee: MARUZEN PETROCHEMICAL CO., LTD., Chuo-ku (JP)

( * ) Notice: Subject to any disclaimer, the term of this patent is extended or adjusted under 35 U.S.C. 154(b) by 0 days.

(21) Appl. No.: 16/331,613

(22) PCT Filed: Sep. 13, 2017

(86) PCT No.: PCT/JP2017/032951
§ 371 (c)(1),
(2) Date: Mar. 8, 2019

(87) PCT Pub. No.: WO2018/051996
PCT Pub. Date: Mar. 22, 2018

(65) Prior Publication Data
US 2019/0210949 A1    Jul. 11, 2019

(30) Foreign Application Priority Data
Sep. 14, 2016 (JP) .............................. JP2016-179078

(51) Int. Cl.
C07C 41/38 (2006.01)
C07C 41/42 (2006.01)
C07C 41/08 (2006.01)
C07C 43/13 (2006.01)
C07C 43/16 (2006.01)
C07B 61/00 (2006.01)

(52) U.S. Cl.
CPC .............. *C07C 41/38* (2013.01); *C07C 41/08* (2013.01); *C07C 41/42* (2013.01); *C07C 43/13* (2013.01); *C07C 43/16* (2013.01); *C07B 61/00* (2013.01)

(58) Field of Classification Search
None
See application file for complete search history.

(56) References Cited

U.S. PATENT DOCUMENTS 2,779,720 A * 1/1957 Tanona ................... C07C 41/42
203/55
2,969,395 A * 1/1961 Nedwick ................. C07C 43/16
564/391
3,287,235 A 11/1966 Statman
3,492,358 A * 1/1970 Gurgiolo ................. C07C 41/38
568/621
3,878,058 A 4/1975 Tanaka et al.
6,090,988 A * 7/2000 Kambe .................... C07C 41/42
502/240
2006/0015131 A1 7/2006 Klass et al.
2010/0249465 A1 9/2010 Tenjimbayashi et al.

FOREIGN PATENT DOCUMENTS

| GB | 787915 | 12/1957 |
| JP | 48 80507 | 10/1973 |
| JP | 10-109952 A | 4/1998 |
| JP | 10-158208 A | 6/1998 |
| JP | 2006-527225 A | 11/2006 |
| JP | 2010-229049 A | 10/2010 |

OTHER PUBLICATIONS

International Search Report dated Dec. 19, 2017 in PCT/JP2017/032951 filed Sep. 13, 2017.
Cullen, A. J. et al., "Highly Selective Reduction of Acyclic β-Alkoxy Ketones to Protected syn-1,3-Diols," Organic Letters, 2004, vol. 6, No. 18, pp. 3143-3145, with Supporting Information (Total 18 pages).
Mikhant'Ev, V. B. et al., "Journal of Applied Chemistry of the USSR," Jan. 1990, vol. 63, No. 1, Part 2, pp. 156-161. (Total 7 page).

(Continued)

*Primary Examiner* — Rosalynd A Keys
(74) *Attorney, Agent, or Firm* — Oblon, McClelland, Maier & Neustadt, L.L.P.

(57) ABSTRACT

To provide a method capable of easily and efficiently removing a 2-alkoxyethanol from a mixture containing the 2-alkoxyethanol and a (2-alkoxyethyl) vinyl ether while suppressing a decrease in the yield of (2-alkoxyethyl) vinyl ether.

A method for removing a 2-alkoxyethanol, including the step of adding one or more azeotropic solvents selected from the group consisting of alkanes having 7 to 8 carbon atoms and cycloalkanes having 7 to 8 carbon atoms to a mixture containing the 2-alkoxyethanol represented by the following formula (1)

$$R\text{—}O\text{—}CH_2CH_2OH \quad (1)$$

where R represents an alkyl group having 1 to 4 carbon atoms, and a (2-alkoxyethyl) vinyl ether represented by the following formula (2)

$$R\text{—}O\text{—}CH_2CH_2O\text{—}CH\text{=}CH_2 \quad (2)$$

where R has the same meaning as R in the formula (1), and subjecting the resulting mixture to azeotropic distillation.

18 Claims, 4 Drawing Sheets

(56) References Cited

OTHER PUBLICATIONS

Suzuki, T. et al., "Syntheses of Monomethoxy Polyethyleneglycol Vinyl Ether Macromonomers and Their Radical Copolymerization with Maleic Anhydride," Journal of Polymer Science, Polymer Chemistry Edition, 1984, vol. 22, pp. 2829-2839. (Total 11 page).
Hirata, M., "Distillation," Chemistry and Biology, 1964, vol. 2, No. 6, pp. 311-316, with Partial translation of p. 313, Azeotropic Distillation (Total 9 page).
Hirose, Y. et al., "Removal of Micro Water in Acetone by Azeotropic Distillation," The Society of Chemical Engineers, Japan, 1970, vol. 34, No. 3, pp. 73-77, with Partial translation of p. 74, Removal of Trace Moisture in Acetone by Azeotropic Distillation (Total 9 page).
Horsley, "Azeotropic Data—lll," Advances in Chemistry, American Chemical Society, 1973, Series 116, pp. 203-206, 254-257, 294-296, 353-354 (Total 13 page).
"Newest Distillation Engineering", M. Hirata, Jan. 1971, Nikkan Kogyo Shimbun., Ltd. Selection of azeotropic agent , w/ English translation 3 pages.
"Newest Distillation Engineering", M. Hirata, Jan. 1971, Nikkan Kogyo Shimbun., Ltd. Selection of azeotropic agent , pp. 58-59 (in Japanese on one page), a cover page and colophon of Hirata (three pages in Japanese), and English translation of Japanese p. 58 of Hirata (one page) (total 5 pages).
Abstract from "Chemical Engineering Handbooks, Basic Edition II", 3rd edition, pp. 11-150-11-151,1984, The society of Chemical Engineer, w/ English translation—3 pages.

\* cited by examiner

METHOD FOR REMOVING OR COLLECTING 2-ALKOXYETHANOL, AND METHOD FOR PRODUCING (2-ALKOXYETHYL) VINYL ETHER

TECHNICAL FIELD

The present invention relates to a method for removing or recovering a 2-alkoxyethanol, and a method for producing a (2-alkoxyethyl) vinyl ether. More specifically, the present invention relates to a method for removing or recovering a 2-alkoxyethanol, from a mixture of 2-alkoxyethanol and (2-alkoxyethyl) vinyl ether such as a crude vinyl ether obtained when the (2-alkoxyethyl) vinyl ether is produced from the 2-alkoxyethanol as a raw material, and a method for producing a (2-alkoxyethyl) vinyl ether using this removal or recovery method.

BACKGROUND ART

Vinyl ethers are generally produced, for example, by addition reaction of alcohol to acetylene, ether exchange reaction between vinyl ether and alcohol using a transition metal complex, for example, as a catalyst, or vinylation reaction of alcohol using vinyl carboxylate.

In any of these methods for producing vinyl ether, alcohol is used as a raw material. When the raw material alcohol remaining in the obtained crude vinyl ether forms an azeotropic mixture with the vinyl ether, it becomes difficult to separate and recover vinyl ether by distillation.

In order to solve the above problem, a method of destroying azeotropy by adding an alkali metal salt has been proposed (Patent Literature 1).

However, in the method of destroying azeotropy by adding an alkali metal salt, there is a problem that an alkali metal alcoholate is generated by reaction with alcohol, which precipitates as a solid in a liquid at the bottom of a distillation column with reduction of a distillation residual liquid, so that it is difficult to put a continuous process into practical use.

There is also known a method of removing alcohol from an azeotropic mixture of which azeotropic composition varies depending on pressure by using two distillation columns and performing distillation under different pressure conditions (for example, Patent Literatures 2 and 3).

However, it was difficult to apply the methods described in Patent Documents 2 and 3 to an azeotropic mixture in which a change in azeotropic composition is small due to pressure, such as an azeotropic mixture of 2-alkoxyethanol and (2-alkoxyethyl) vinyl ether. Furthermore, in this method, since the main component of the azeotropic mixture distilled from the upper portion of the second distillation column is vinyl ether, there is a problem that the yield of vinyl ether decreases.

Also, a method has been proposed in which raw material alcohol is reacted with vinyl ether as a product to subject the reaction mixture to an acetalization, and acetal and vinyl ether are separated by distillation (Patent Literature 4).

However, since the vinyl ether in an amount equivalent to the alcohol is lost by the reaction, the method described in Patent Literature 4 also has a problem that the yield of vinyl ether decreases.

In addition, as a method of separating vinyl ether and raw material alcohol, a method of performing distillation using glycol or glycol monoether containing water as an extraction solvent (Patent Literature 5), a method of performing distillation using water or a mixed solvent of water and phenol as an extraction solvent (Patent Literature 6) have been reported. In any of these methods, an azeotropic mixture of water and vinyl ether is obtained from the top of the column, and separated into an oil phase and an aqueous phase by a decanter. However, since any of these methods use water, there is a problem that the vinyl ether is lost by hydrolysis and thus the yield decreases. Furthermore, since the raw material alcohol recovered from the bottom of the column contains the adequate amount of water, it requires a lot of energy to recover and reuse the raw material alcohol, and a large amount of wastewater treatment is further required.

On the other hand, as a separation method without using water, a method using only glycol monoether as an extraction solvent (Patent Literature 7) and a method using a polar solvent such as diol or dimethyl sulfoxide (Patent Literature 8) are known. However, these methods have a low selectivity in separating 2-alkoxyethanol and (2-alkoxyethyl) vinyl ether, and require a very large amount of heat in order to increase the relative volatility even just a little.

Furthermore, regardless of whether water is used or not, the extractive distillation method generally uses a large amount of extraction solvent, so that solvent cost, equipment cost, energy cost increases, which makes industrial implementation difficult.

CITATION LIST

Patent Literatures

Patent Literature 1: GB 787,915 B
Patent Literature 2: JP H10-109952 A
Patent Literature 3: JP 2006-527225 A
Patent Literature 4: JP 2010-229049 A
Patent Literature 5: U.S. Pat. No. 2,779,720
Patent Literature 6: U.S. Pat. No. 3,287,235
Patent Literature 7: JP S48-80507 A
Patent Literature 8: JP H10-158208 A

SUMMARY OF INVENTION

Technical Problem

In addition, the raw material alcohol has a boiling point higher than that of vinyl ether as a product. Therefore, when the raw material alcohol forms an azeotropic mixture with vinyl ether, in order to remove the raw material alcohol by azeotropic distillation using a third component (azeotropic solvent), it is important for the azeotropic solvent to form an azeotropic mixture with the raw material alcohol and to exhibit an azeotropic point sufficiently lower than the boiling point of vinyl ether. However, there is little precedent that raw material alcohol is removed by such azeotropic distillation method. Particularly, in the case of a high-boiling vinyl ether having a boiling point more than 100° C. at normal pressure, such as (2-alkoxyethyl) vinyl ether, distillation is often performed under reduced pressure and the boiling point difference is small, so that removal of the raw material alcohol by azeotropic distillation using an azeotropic solvent becomes further difficult. Furthermore, even when a system that forms azeotropy in a two-component system is known, the azeotropic behavior greatly differs in the presence of the third component, so that the optimum azeotropic solvent in a certain system may not be necessarily optimal in another system, and it is very difficult to predict an optimal azeotropic solvent in a specific system.

An object to be solved by the present invention is to provide a method capable of easily and efficiently removing a 2-alkoxyethanol from a mixture containing the 2-alkoxyethanol and a (2-alkoxyethyl) vinyl ether while suppressing a decrease in the yield of (2-alkoxyethyl) vinyl ether.

Solution to Problem

Therefore, the present inventors have conducted extensive studies on the separation of (2-alkoxyethyl) vinyl ether and 2-alkoxyethanol that is a raw material thereof. As a result, it found that, when a specific azeotropic solvent is used, the 2-alkoxyethanol can be easily and efficiently removed from the mixture by azeotropic distillation, and the decrease in the yield of (2-alkoxyethyl) vinyl ether can also be suppressed. Thus, they have completed the present invention.

That is, the present invention provides the following <1> to <9>.

<1> A method for removing a 2-alkoxyethanol represented by the following formula (1) (hereinafter also referred to as 2-alkoxyethanol (1))

$$R\text{—}O\text{—}CH_2CH_2OH \qquad (1)$$

where R represents an alkyl group having 1 to 4 carbon atoms, including the step of adding one or more azeotropic solvent selected from the group consisting of alkanes having 7 to 8 carbon atoms and cycloalkanes having 7 to 8 carbon atoms to a mixture containing the 2-alkoxyethanol and a (2-alkoxyethyl) vinyl ether represented by the following formula (2) (hereinafter also referred to as (2-alkoxyethyl) vinyl ether (2))

$$R\text{—}O\text{—}CH_2CH_2O\text{—}CH\text{=}CH_2 \qquad (2)$$

where R has the same meaning as R in the formula (1), and subjecting the resulting mixture to azeotropic distillation (hereinafter also referred to as the removal method of the present invention).

<2> A method for recovering a 2-alkoxyethanol, including the steps of adding one or more azeotropic solvents selected from the group consisting of alkanes having 7 to 8 carbon atoms and cycloalkanes having 7 to 8 carbon atoms to a mixture containing a 2-alkoxyethanol (1) and a (2-alkoxyethyl) vinyl ether (2), and subjecting the resulting mixture to azeotropic distillation, and separating the azeotropic mixture distilled by the azeotropic distillation into a 2-alkoxyethanol phase and an azeotropic solvent phase by liquid-liquid separation (hereinafter also referred to as the recovery method of the present invention).

<3> The method according to <1> or <2>, wherein the mixture containing the 2-alkoxyethanol (1) and the (2-alkoxyethyl) vinyl ether (2) is a reaction mixture obtained by a vinyl etherification reaction using the 2-alkoxyethanol (1) as a raw material alcohol.

<4> A method for producing a (2-alkoxyethyl) vinyl ether (2) using a 2-alkoxyethanol (1) as a raw material alcohol, including a vinyl etherification step of subjecting the raw material alcohol to vinyl etherification to obtain a reaction mixture containing an unreacted raw material alcohol and the (2-alkoxyethyl) vinyl ether (2), and a raw material alcohol removal step of adding one or more azeotropic solvent selected from the group consisting of alkanes having 7 to 8 carbon atoms and cycloalkanes having 7 to 8 carbon atoms to the reaction mixture and removing the raw material alcohol by azeotropic distillation (hereinafter also referred to as the production method of the present invention).

<5> A method for producing a (2-alkoxyethyl) vinyl ether (2) using a 2-alkoxyethanol (1) as a raw material alcohol, including a vinyl etherification step of subjecting the raw material alcohol to vinyl etherification in the presence of a catalyst to obtain a reaction mixture containing an unreacted raw material alcohol and the (2-alkoxyethyl) vinyl ether (2), a catalyst removal step of removing the catalyst from the reaction mixture obtained in the vinyl etherification step, and a raw material alcohol removal step of adding one or more azeotropic solvent selected from the group consisting of alkanes having 7 to 8 carbon atoms and cycloalkanes having 7 to 8 carbon atoms to the reaction mixture and removing the raw material alcohol by azeotropic distillation.

<6> The production method according to <4> or <5>, further including a liquid-liquid separation step of separating the azeotropic mixture distilled in the raw material alcohol removal step into a raw material alcohol phase and an azeotropic solvent phase by liquid-liquid separation, and an azeotropic solvent feeding step of feeding at least a part of the azeotropic solvent phase separated in the liquid-liquid separation step to the raw material alcohol removal step.

<7> The production method according to <6>, further including a raw material alcohol feeding step of feeding at least a part of the raw material alcohol phase separated in the liquid-liquid separation step to the vinyl etherification step.

<8> The method according to any one of <1> to <7>, in which the azeotropic solvent is one or more azeotropic solvent selected from the group consisting of normal heptane and isooctane.

<9> The method according to any one of <1> to <8>, wherein R in the formulae (1) and (2) is a methyl group or an ethyl group.

Advantageous Effects of Invention

According to the removal method and the recovery method of the present invention, a 2-alkoxyethanol can be easily and efficiently removed and recovered from a mixture containing the 2-alkoxyethanol and a (2-alkoxyethyl) vinyl ether while suppressing a decrease in the yield of (2-alkoxyethyl) vinyl ether.

According to the production method of the present invention, the raw material alcohol can be easily and efficiently removed from a crude vinyl ether while suppressing a decrease in the yield of (2-alkoxyethyl) vinyl ether, and high purity of the (2-alkoxyethyl) vinyl ether can be industrially advantageously produced.

DETAILED DESCRIPTION OF THE INVENTION

[Method for Removing 2-Alkoxyethanol]

Figure 1:
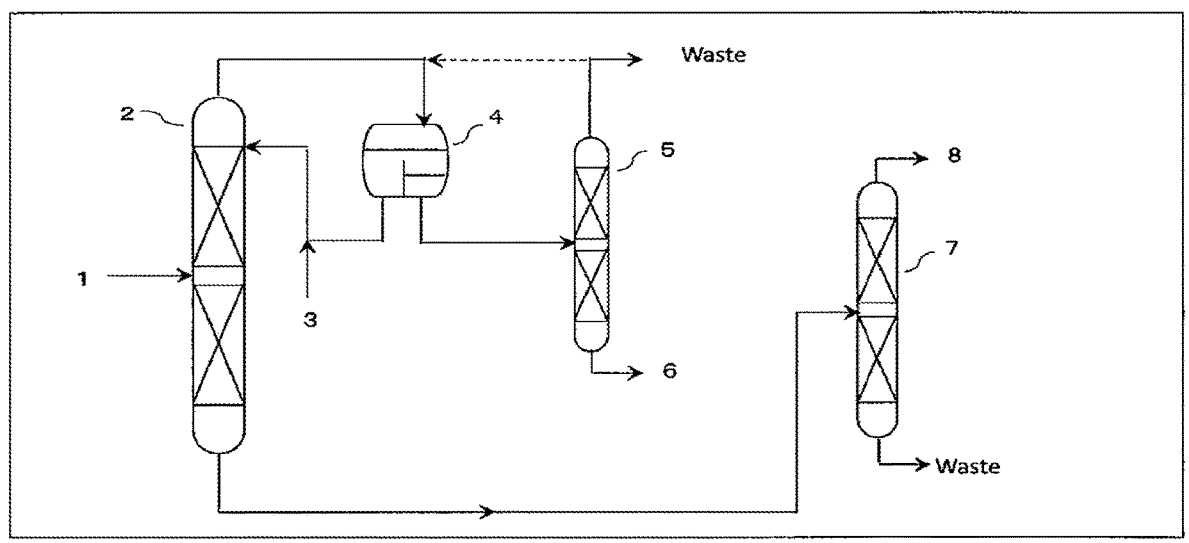
FIG. 1 is a process chart showing an example of raw material alcohol removal step, liquid-liquid separation step, azeotropic solvent feeding step, raw material alcohol feeding step, and rectification step in the production method of the present invention.

The removal method of the present invention removes a 2-alkoxyethanol (1) from a mixture containing the 2-alkoxyethanol (1) and a (2-alkoxyethyl) vinyl ether (2) (for example, a mixed solution of a crude vinyl ether).

In the formulae (1) and (2), R represents an alkyl group having 1 to 4 carbon atoms. The number of carbon atoms in the alkyl group is preferably 1 or 2. The alkyl group may also be linear or branched. Examples of the alkyl group include a methyl group, an ethyl group, an n-propyl group, an isopropyl group, an n-butyl group, an isobutyl group, a sec-butyl group, and a tert-butyl group. Among them, a methyl group and an ethyl group are preferable, and a methyl group is particularly preferable.

Specific examples of the 2-alkoxyethanol (1) include 2-methoxyethanol, 2-ethoxyethanol, 2-propoxyethanol, 2-isopropoxyethanol, 2-butoxyethanol, 2-isobutoxyethanol, 2-sec-butoxyethanol, and 2-tert-butoxyethanol, and one of them may be used alone, or two or more of them may be used in combination.

Among them, the removal method of the present invention is suitable for removal of 2-methoxyethanol and 2-ethoxyethanol.

The content of 2-alkoxyethanol (1) is preferably 1 to 40% by mass, more preferably 1.5 to 30% by mass, further preferably 2 to 20% by mass, and particularly preferably 3 to 15% by mass, in the mixture.

Also, specific examples of (2-alkoxyethyl) vinyl ether (2) include (2-methoxyethyl) vinyl ether, (2-ethoxyethyl) vinyl ether, (2-propoxyethyl) vinyl ether, (2-isopropoxyethyl) vinyl ether, (2-butoxyethyl) vinyl ether, (2-isobutoxyethyl) vinyl ether, (2-sec-butoxyethyl) vinyl ether, and (2-tert-butoxyethyl) vinyl ether, and one of them may be used alone, or two or more of them may be used in combination.

Among them, (2-methoxyethyl) vinyl ether and (2-ethoxyethyl) vinyl ether are preferable.

The content of (2-alkoxyethyl) vinyl ether (2) is preferably 60 to 99% by mass, more preferably 70 to 98.5% by mass, further preferably 80 to 98% by mass, and particularly preferably 85 to 97% by mass, in the mixture.

The mass ratio of the content of 2-alkoxyethanol (1) to (2-alkoxyethyl) vinyl ether (2) [(1):(2)] in the mixture is preferably 1:99 to 40:60, more preferably 1.5:98.5 to 30:70, further preferably 2:98 to 20:80, and particularly preferably 3:97 to 15:85.

In addition, the total content of 2-alkoxyethanol (1) and (2-alkoxyethyl) vinyl ether (2) is preferably 80 to 100% by mass, more preferably 90 to 100% by mass, and particularly preferably 95 to 100% by mass, in the mixture.

As the mixture containing the 2-alkoxyethanol (1) and the (2-alkoxyethyl) vinyl ether (2), a reaction mixture obtained by a vinyl etherification reaction using the 2-alkoxyethanol (1) as a raw material alcohol is preferable. Examples of the reaction mixture include, for example, the reaction mixture obtained by the vinyl etherification step in the production method of the present invention and the reaction mixture from which the catalyst have been removed.

Further, the removal method of the present invention performs azeotropic distillation using one or more azeotropic solvent selected from the group consisting of alkanes having 7 to 8 carbon atoms and cycloalkanes having 7 to 8 carbon atoms.

Since the mixture containing the 2-alkoxyethanol (1) and the (2-alkoxyethyl) vinyl ether (2) forms an azeotropic mixture, it is difficult to sufficiently remove the 2-alkoxyethanol (1) by a usual distillation operation. Meanwhile, by performing azeotropic distillation using the above azeotropic solvent, the 2-alkoxyethanol (1) can be easily and efficiently removed while suppressing a decrease in the yield of (2-alkoxyethyl) vinyl ether (2). In addition, the azeotropic solvent is also excellent in thermal stability and safety, low in toxicity and corrosiveness, and is inexpensive, so that the removal method of the present invention is suitable for industrial use.

Alkanes and cycloalkanes having 6 or less carbon atoms are poor in phase separation property with the 2-alkoxyethanol (1) and cannot be recovered and reused by liquid-liquid separation to be described later, which is industrially disadvantageous. Also, alkanes and cycloalkane having 9 or more carbon atoms have a high boiling point, and it is difficult to efficiently remove the 2-alkoxyethanol (1) by azeotropic distillation even when these are used as an azeotropic solvent.

The alkane having 7 to 8 carbon atoms may be linear or branched. The cycloalkane having 7 to 8 carbon atoms may be an alkyl group substituted on the ring as long as the total carbon number is 7 to 8.

Examples of the azeotropic solvent include normal heptane, 2-methylhexane, 3-methylhexane, 2,2-dimethylpentane, 2,3-dimethylpentane, 2,4-dimethylpentane, 3,3-dimethylpentane, 3-ethylpentane, 2,2,3-trimethylbutane, methylcyclohexane, isooctane, and 2,5-dimethylhexane. One of them may be used alone, or two or more of them may be used in combination.

Among them, in view of excellent removal performance of the 2-alkoxyethanol (1), normal heptane, 2-methylhexane, 3-methylhexane, 2,2-dimethylpentane, 2,3-dimethylpentane, 2,4-dimethylpentane, 3,3-dimethylpentane, 3-ethylpentane, 2,2,3-trimethylbutane, methylcyclohexane and isooctane are preferable, and normal heptane, isooctane and methylcyclohexane are more preferable, and in view of excellent separability of the 2-alkoxyethanol (1) in the liquid-liquid separation to be described later, normal heptane and isooctane are particularly preferable. Here, isooctane is 2,2,4-trimethylpentane or a branched C8 isomer mixture mainly composed of the same.

The use amount of the azeotropic solvent is usually 0.01 to 50 times by mass, preferably 0.1 to 10 times by mass, more preferably 1 to 8 times by mass, and particularly preferably 4 to 6 times by mass, relative to the 2-alkoxyethanol (1). By setting the use amount of the azeotropic solvent with respect to the 2-alkoxyethanol (1) to 4 times by mass or more, the 2-alkoxyethanol (1) can be sufficiently removed and high purity vinyl ether can be obtained. Also, by setting the use amount to 10 times by mass or less, the solvent cost can be suppressed, deterioration of operation efficiency and controllability of the distillation column can be prevented, and mixing of the azeotropic solvent into the (2-alkoxyethyl) vinyl ether (2) can be also prevented.

In addition, azeotropic distillation is usually performed using a distillation column (azeotropic column). The distillation column may be, for example, any of a packed column, a plate column and a bubble cap column, and the plate number of the distillation column is preferably 1 to 100, and more preferably 5 to 70, in terms of theoretical plate number. Further, the column top temperature of the distillation column is preferably in the range of 40 to 150° C., the column bottom temperature is preferably in the range of 50 to 200° C., and the reflux ratio is preferably 1 to 50.

Distillation may be any of atmospheric distillation, pressure distillation and reduced-pressure distillation, and atmospheric distillation and reduced-pressure distillation are preferable, and reduced-pressure distillation is more preferable, in terms of removal efficiency of 2-alkoxyethanol (1). Specifically, the distillation pressure is preferably 1 kPa to atmospheric pressure, and more preferably 10 to 100 kPa, and in terms of energy efficiency, it is further preferably more than 40 kPa and 90 kPa or less, and particularly preferably 50 to 80 kPa. Also, the distillation temperature is preferably in the range of 50 to 200° C., and more preferably in the range of 60 to 150° C.

Further, the distillation system may be any of batch, semi-batch and continuous systems, and a continuous system is preferred. Distillation is particularly preferably performed continuously under reduced pressure.

When azeotropic distillation is performed using the above distillation column, the 2-alkoxyethanol (1) distills from the top of the column as an azeotropic mixture containing the 2-alkoxyethanol (1) and the azeotropic solvent, and the (2-alkoxyethyl) vinyl ether (2) is extracted from the bottom of the distillation column as bottoms (extraction liquid).

Azeotropic distillation can be performed until the concentration of 2-alkoxyethanol (1) in the above bottoms reaches a desired value (for example, less than to by mass). The content of 2-alkoxyethanol (1) can be confirmed by a known method, for example, gas chromatography. The bottoms may be further rectified to remove heavy components, for example.

[Method for Recovering 2-Alkoxyethanol]

The recovery method of the present invention includes a step of adding one or more azeotropic solvents selected from the group consisting of alkanes having 7 to 8 carbon atoms and cycloalkanes having 7 to 8 carbon atoms to a mixture containing the 2-alkoxyethanol (1) and the (2-alkoxyethyl) vinyl ether (2), and subjecting the resulting mixture to azeotropic distillation. The azeotropic distillation may be performed in the same manner as in the azeotropic distillation in the removal method of the present invention.

Further, the recovery method of the present invention includes a step of separating the azeotropic mixture distilled by the azeotropic distillation into a 2-alkoxyethanol phase and an azeotropic solvent phase by liquid-liquid separation. The 2-alkoxyethanol phase refers to a phase containing the 2-alkoxyethanol more than the azeotropic solvent phase, and the azeotropic solvent phase refers to a phase containing the azeotropic solvent more than the 2-alkoxyethanol phase.

Since the azeotropic solvent used in the present invention has low solubility in the 2-alkoxyethanol (1), the azeotropic mixture distilled from the top of the column is released by dissipation in the receiver of the distillate, thereby separating into two phases. Therefore, it is possible to easily separate and recover the 2-alkoxyethanol phase and the azeotropic solvent phase by the liquid-liquid separation. They can also be used as a raw material alcohol for the (2-alkoxyethyl) vinyl ether (2) and an azeotropic solvent.

The liquid-liquid separation temperature is usually 50° C. or less, and preferably 40° C. or less, and in terms of energy efficiency, it is more preferably less than 40° C., further preferably 35° C. or less, and particularly preferably 0 to 30° C. Also, by setting the temperature of the liquid-liquid separation to such a range and setting the distillation pressure in the azeotropic distillation step to the above range, the energy efficiency can be greatly improved.

The liquid-liquid separation can be performed by a known liquid separation operation, for example, a method of separating by a liquid-liquid separator such as a decanter. Further, the recovered 2-alkoxyethanol phase may be purified by distillation, for example.

[Method for Producing (2-Alkoxyethyl) Vinyl Ether]

<Vinyl Etherification Step>

The vinyl etherification step is a step of subjecting the raw material alcohol (2-alkoxyethanol (1)) to vinyl etherification, to obtain a reaction mixture containing an unreacted raw material alcohol and the (2-alkoxyethyl) vinyl ether (2).

The method for obtaining the (2-alkoxyethyl) vinyl ether (2); from the raw material alcohol is not particularly limited as long as it is a known vinyl etherification reaction: Examples of the method include a method of reacting the 2-alkoxyethanol (1) with a compound having a carbon-carbon double bond or a carbon-carbon triple bond in the molecule, and more specifically, examples include, (A) ether exchange reaction between vinyl ether and alcohol, (B) vinylation reaction of alcohol using vinyl carboxylate, and (C) addition reaction of alcohol to acetylene. In addition; it is preferable to perform vinyl etherification in the presence of a catalyst.

Hereinafter, the reactions (A) to (C) will be described in detail.

(A) Ether Exchange Reaction

Examples of the ether exchange reaction (A) include a method of reacting the 2-alkoxyethanol (1) with a vinyl ether different from the target vinyl ether in the presence of a transition metal complex catalyst.

The vinyl ether used in the ether exchange reaction (A) is preferably an alkyl vinyl ether such as methyl vinyl ether, ethyl vinyl ether, n-propyl vinyl ether or n-butyl vinyl ether, in that it is inexpensive and easily available as compared with the target vinyl ether.

As the transition metal complex catalyst, one known as a catalyst for vinyl ether exchange reaction can be used. Examples thereof include 1,10-phenanthroline complexes of palladium such as palladium acetate-1,10-phenanthroline complex, and palladium chloride-1,10-phenanthroline complex; cobalt carbonyl complexes such as $Co(CH_3COCHCOCH_3)_2$, $Co(CH_3COCHCOCH_3)_3$, $Co(CH_3COCHCOCH_3)_2 \cdot 2H_2O$, and $Co_2(CO)_8$.

Also, an organic solvent may be used in the ether exchange reaction (A). Examples of the organic solvent include saturated hydrocarbon solvents such as pentane, hexane, heptane, cyclopentane and cyclohexane; ether solvents such as dioxane, diethyl ether, diisopropyl ether, methyl-tert-butyl ether, tetrahydrofuran, diethylene glycol dimethyl ether, diethylene glycol diethyl ether, triethylene glycol dimethyl ether and triethylene glycol diethyl ether; aromatic hydrocarbon solvents such as benzene and toluene; and sulfonyl solvents such as sulfolane. One of them may be used alone, or two or more of them may be used in combination.

The reaction temperature in the ether exchange reaction (A) is usually in the range of −20 to 150° C., and from the viewpoint of the reaction rate and side reaction suppression, it is preferably in the range of 0 to 100° C., and more preferably in the range of 20 to 50° C. Also, the reaction time differs depending on the reaction conditions, but is usually about 10 minutes to 48 hours.

(B) Vinylation Reaction

Examples of the vinylation reaction (B) include a method of reacting the 2-alkoxyethanol (1) with a carboxylic acid vinyl ester in the presence of a transition metal complex catalyst and a basic compound.

Examples of the carboxylic acid vinyl ester include vinyl acetate, vinyl propionate, vinyl formate, and vinyl benzoate.

As the transition metal complex catalyst, one known as a catalyst for vinyl exchange reaction can be used. Examples thereof include iridium complexes such as di-μ-chlorotetrakis(cyclooctene)diiridium(I), di-μ-chlorotetrakis(ethylene)diiridium(I), di-μ-chlorobis(1,5-cyclooctadiene)diiridium (I), bis(1,5-cyclooctadiene)iridium tetrafluoroborate, and (1,5-cyclooctadiene)(acetonitrile)iridium tetrafluoroborate.

Examples of the basic compound include hydroxides, carbonates, and hydrogen carbonates of alkali metals such as sodium and potassium. In addition, since the vinylation reaction (B) is an equilibrium reaction, it is preferable to carry out the reaction while removing water by-produced by a reaction between the carboxylic acid and the basic compound, out of the system.

Also, an organic solvent may be used in the vinylation reaction (B). Examples of the organic solvent include the same ones as those used in the ether exchange reaction (A).

The reaction temperature of the vinylation reaction (B) is usually in the range of 50 to 170° C., and from the viewpoint of the reaction rate and side reaction suppression, it is preferably in the range of 70 to 150° C., and more preferably in the range of 90 to 130° C. Also, the reaction time differs depending on the reaction conditions, but is usually about 10 minutes to 48 hours.

(C) Addition Reaction to Acetylene

Examples of the addition reaction to acetylene (C) include a method of reacting the 2-alkoxyethanol (1) with acetylene in the presence of an alkali metal alcoholate catalyst.

The alkali metal alcoholate catalyst is a compound synthesized from an alkali metal hydroxide and the 2-alkoxyethanol (1), and in terms of handling property, it is preferably one soluble in alcohol. Specific examples of the alkali metal hydroxide include sodium hydroxide, potassium hydroxide, rubidium hydroxide, and cesium hydroxide, and one of them may be used alone, or two or more of them may be used in combination.

In the reaction (C), an organic solvent may be used. As the organic solvent, for example, an aprotic polar solvent which is miscible with the 2-alkoxyethanol (1) and dissolves the alkali metal alcoholate catalyst is preferable. Examples thereof include amide type solvents such as dimethylacetamide, 2-pyrrolidone, N-methyl-2-pyrrolidone, and 1,3-dimethyl-2-imidazolidinone; sulfur-containing compound type solvents such as sulfolane and dimethyl sulfoxide; and glycol dialkyl ether type solvents such as diethylene glycol dimethyl ether, diethylene glycol diethyl ether, triethylene glycol dimethyl ether, and triethylene glycol diethyl ether, and one of them may be used alone, or two or more of them may be used in combination.

The reaction temperature of the reaction (C) is usually in the range of 80 to 200° C., and from the viewpoint of the reaction rate and side reaction suppression, it is more preferably in the range of 100 to 180° C. The higher the reaction pressure, the higher the reaction rate. However, in order to prevent decomposition and explosion of acetylene, the reaction pressure is preferably 0.3 MPa or less. Also, the reaction time differs depending on the reaction conditions, but is usually about 10 minutes to 48 hours.

Among the reactions (A) to (C), the addition reaction to acetylene of (C) is preferable in that the yield is high, the raw materials are inexpensive, and no special catalyst is required.

<Catalyst Removal Step>

In the case where the vinyl etherification reaction is carried out in the presence of a catalyst, it is preferable to remove the catalyst and the like from the reaction mixture obtained in the vinyl etherification step before subjecting to azeotropic distillation.

Removal of the catalyst and the like can be carried out by a known method such as solid-liquid separation (in the case of a solid catalyst or a supported catalyst) such as solvent extraction, distillation, or filtration. Among these methods, the method by distillation is preferable in that the catalyst can be easily separated and the raw material alcohol can be reduced in advance. In addition, even when the catalyst is removed by a method other than distillation, the raw material alcohol in the reaction mixture may be reduced by further distillation.

The distillation column used in distillation for removal of the catalyst or concentration after removal of the catalyst (hereinafter referred to as "preliminary distillation") may be, for example, any of a packed column, a plate column and a bubble bell column, and the plate number of the distillation column is, for example, 1 to 100, and preferably 5 to 50, in terms of theoretical plate number.

The preliminary distillation can be performed under any of normal pressure, under pressure and under reduced pressure, and preferably under normal pressure or under reduced pressure. Specifically, the pressure is preferably 1 kPa to atmospheric pressure, and more preferably 10 to 100 kPa.

Further, the distillation system may be any of a batch system, a semi-batch system and a continuous system, and more preferably a continuous system under reduced pressure.

The distillate obtained by preliminary distillation is a mixture containing the 2-alkoxyethyl vinyl ether (2) and its raw material alcohol. The composition of the mixture (such as the content of raw material alcohol and 2-alkoxyethyl vinyl ether (2) in the mixture) is preferably the same as that of the mixture containing the 2-alkoxyethanol (1) and the (2-alkoxyethyl) vinyl ether (2) in the removal method of the present invention.

<Raw Material Alcohol Removal Step>

The raw material alcohol removal step is a step of adding one or more azeotropic solvents selected from the group consisting of alkanes having 7 to 8 carbon atoms and cycloalkanes having 7 to 8 carbon atoms to the reaction mixture (crude vinyl ether) obtained in the vinyl etherification step or catalyst removal step, and removing the raw material alcohol by azeotropic distillation. The removal of the raw material alcohol may be carried out in the same manner as in the azeotropic distillation in the removal method of the present invention.

<Liquid-Liquid Separation Step>

The production method of the present invention preferably includes a liquid-liquid separation step of separating an azeotropic mixture containing the raw material alcohol and the azeotropic solvent, distilled in the raw material alcohol removal step into a raw material alcohol phase and an azeotropic solvent phase by liquid-liquid separation. By this constitution, it becomes possible to reuse the raw material alcohol and the azeotropic solvent contained in the azeotropic mixture.

In the liquid-liquid separation step, separation and recovery may be carried out in the same manner as in the liquid-liquid separation in the recovery method of the present invention.

<Azeotropic Solvent Feeding Step>

Further, the production method of the present invention preferably includes an azeotropic solvent feeding step of feeding at least a part of the azeotropic solvent phase separated in the liquid-liquid separation step to a raw material alcohol removal step. With this configuration, the production cost of vinyl ether can be suppressed.

Specific examples include a method in which the azeotropic solvent phase separated by a decanter is extracted, fed to a distillation column (azeotropic column), and circulated.

<Raw Material Alcohol Feeding Step>

In addition, the production method of the present invention preferably includes a raw material alcohol feeding step of feeding at least a part of the raw material alcohol phase separated in the liquid-liquid separation step to the vinyl etherification step. With this configuration, the production cost of vinyl ether can be suppressed.

Alternatively, at least a part of the raw material alcohol phase may be purified and then fed to the vinyl etherification step. Specific examples include a method in which at least a part of the raw material alcohol phase after the liquid-liquid separation is introduced into a second distillation column (raw material recovery column) to extract the azeotropic solvent from the top of the column, and to recover the raw material alcohol from the bottom of the column, and the recovered raw material alcohol is fed to the vinyl etherification step and reused as a raw material. As a result, the recovery rate of the raw material alcohol can be made 90% or more, and the loss becomes small.

Also, the azeotropic solvent extracted from the top of the second distillation column can be reintroduced to the decanter and circulated to the azeotropic column.

<Rectification Step>

Further, the production method of the present invention may include a rectification step of rectifying the high purity of (2-alkoxyethyl) vinyl ether (2) obtained in the raw material alcohol removal step.

Specific examples include a method in which the bottoms extracted from the bottom of the azeotropic column are introduced into a third distillation column (rectification column) to obtain purified vinyl ether from the top of the column. When a rectification column is provided, operating conditions are set so that the purity of the vinyl ether after rectification falls within a desired range (for example, 99% by mass or more).

Hereinafter, the production method of the present invention will be described in more detail with reference to FIG. 1.

FIG. 1 is a process chart showing an example of the raw material alcohol removal step, the liquid-liquid separation step, the azeotropic solvent feeding step, the raw material alcohol feeding step, and the rectification step in the production method of the present invention.

The apparatus shown in FIG. 1 includes an azeotropic column 2, a path for leading an azeotropic mixture containing the raw material alcohol and the azeotropic solvent distilled from the top of the azeotropic column 2 to a decanter 4, the decanter 4, a path for returning at least a part of the azeotropic solvent phase separated in the decanter 4 to the azeotropic column 2, a raw material recovery column 5, a path for feeding at least a part of the raw material alcohol phase separated in the decanter 4 to the raw material recovery column, a rectification column 7, and a path for feeding bottoms ((2-alkoxyethyl) vinyl ether (2) from which the raw material alcohol has been removed) extracted from the bottom of the azeotropic column 2 to the rectification column 7. The azeotropic column 2, the raw material recovery column 5 and the rectification column 7 may each include a condenser at the top of the column and a reboiler at the bottom of the column (not shown).

A crude vinyl ether 1 containing the (2-alkoxyethyl) vinyl ether (2) and its raw material alcohol is continuously fed to a middle stage of the azeotropic column 2. Further, the azeotropic solvent 3 is continuously fed to the upper stage than the feed stage of the crude vinyl ether 1.

The azeotropic mixture containing the raw material alcohol and the azeotropic solvent is distilled from the top of the azeotropic column 2, and the (2-alkoxyethyl) vinyl ether (2) from which the raw material alcohol has been removed is continuously extracted as bottoms from the bottom of the column. The distillation temperature and pressure are controlled so that the concentration of the raw material alcohol in the bottoms falls within a desired range (for example, less than 1%).

The azeotropic mixture distilled from the top of the azeotropic column 2 is separated into an azeotropic solvent phase and a raw material alcohol phase by liquid-liquid separation in the decanter 4 provided in a circulation path. At least a part of the azeotropic solvent phase is returned from the circulation path to the azeotropic column 2. Meanwhile, a path for returning at least a part of the azeotropic solvent phase to the azeotropic column 2 is provided with a means for feeding the azeotropic solvent 3 into the circulation path, and the feed amount from the outside of the azeotropic solvent 3 and the circulation amount from the decanter 4 is controlled so that the ratio of the retention amount of the azeotropic solvent in the azeotropic column 2 to the retention amount of the raw material alcohol in the azeotropic column 2 falls within a desired range.

On the other hand, at least a part of the raw material alcohol phase is fed to the raw material recovery column 5, light components such as azeotropic solvents are removed, and the raw material alcohol 6 is recovered from the bottom of the column. The recovered raw material alcohol 6 is provided as a synthesis raw material of the (2-alkoxyethyl) vinyl ether (2) to the vinyl etherification step (not shown).

Further, the bottoms from the bottom of the azeotropic column 2 are purified in the rectification column 7 to obtain a product vinyl ether 8.

Examples

Hereinbelow, the present invention will be described in detail by way of examples thereof. It should be noted, however, that the present invention is not limited to these examples.

In the examples, gas chromatography was used for composition analysis of the reaction liquid and the like. The analysis conditions are as follows.

Apparatus: Product name "GC-2014AFSC" (manufactured by Shimadzu Corporation)

Detector: FID

INJ Temperature: 240° C.

DET Temperature: 240° C.

Sample volume: 0.1 μL

Linear velocity: 25.0 cm/sec

Split ratio: 5

Column: Rtx-WAX (30 m, 0.32 mm ID, 0.5 μm, manufactured by Restek Corporation)

Column temperature conditions: hold at 70° C. for 2 minutes→heated at 10° C./min→hold at 240° C. for 6 minutes (for 25 minutes in total)

Reference Example 1: Gas-Liquid Equilibrium (60 kPa) of (2-methoxyethyl) Vinyl Ether and 2-methoxyethanol 5 mL of 2-methoxyethanol and 150 mL of (2-methoxyethyl) vinyl ether were charged into an Osmer equilibrium distillation apparatus, and after adjusting the pressure to 60 kPa, heating was started. From the start of reflux, the equilibrium state was maintained for about 2 hours (5 times or more the receiver retention time). A vapor phase condensate and a liquid phase were sampled, and their compositions were analyzed.

Next, 5 mL of 2-methoxyethanol was added to the system, and the same operation was carried out.

Subsequently, the addition of 2-methoxyethanol into the system was repeated, and a gas-liquid equilibrium diagram of (2-methoxyethyl) vinyl ether and 2-methoxyethanol at 60 kPa was created.

Figure 2:
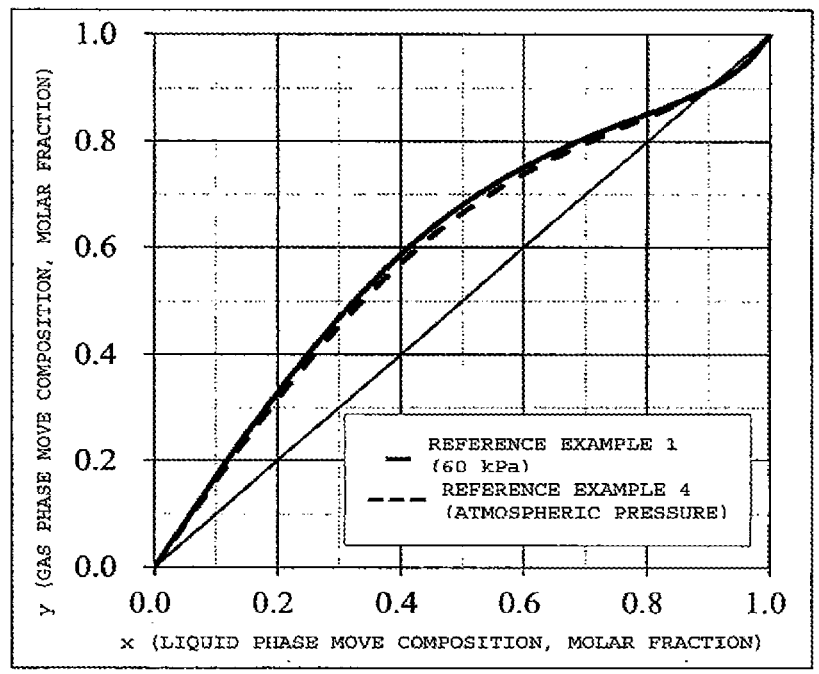
FIG. 2 is a graph showing gas-liquid equilibrium curves (XY diagrams) of mixtures of (2-methoxyethyl) vinyl ether and 2-methoxyethanol.

The gas-liquid equilibrium diagram of (2-methoxyethyl) vinyl ether and 2-methoxyethanol at 60 kPa is shown in FIG. 2. Meanwhile, MOVE in FIG. 2 means (2-methoxyethyl) vinyl ether.

The composition at the intersection of the gas-liquid equilibrium line and a diagonal line, that is, the composition at the azeotropic point was 93.5% by mass of (2-methoxyethyl) vinyl ether and 6.5% by mass of 2-methoxyethanol, and the temperature at that time was 92° C. The results are shown in Table 1.

As can be seen from FIG. 2, due to azeotropy of (2-methoxyethyl) vinyl ether with 2-methoxyethanol as a raw material, general distillation purification is difficult.

Reference Example 2: Gas-Liquid Equilibrium (26.7 kPa) of (2-methoxyethyl) Vinyl Ether and 2-methoxyethanol The same operation as in Reference Example 1 was carried out except that the pressure was changed to 26.7 kPa.

The composition at the azeotropic point was 93.7% by mass of (2-methoxyethyl) vinyl ether and 6.3% by mass of 2-methoxyethanol, and the temperature at that time was 70° C. The results are shown in Table 1.

Reference Example 3: Gas-Liquid Equilibrium (40 kPa) of (2-methoxyethyl) Vinyl Ether and 2-methoxyethanol The same operation as in Reference Example 1 was carried out except that the pressure was changed to 40 kPa.

The composition at the azeotropic point was 93.8% by mass of (2-methoxyethyl) vinyl ether and 6.2% by mass of 2-methoxyethanol, and the temperature at that time was 81° C. The results are shown in Table 1.

Reference Example 4: Gas-Liquid Equilibrium (Atmospheric Pressure) of (2-methoxyethyl) Vinyl Ether and 2-methoxyethanol The same operation as in Reference Example 1 was carried out except that the pressure was changed to atmospheric pressure.

The gas-liquid equilibrium diagram of (2-methoxyethyl) vinyl ether and 2-methoxyethanol under atmospheric pressure is shown in FIG. 2.

The composition at the azeotropic point was 91.0% by mass of (2-methoxyethyl) vinyl ether and 9.0% by mass of 2-methoxyethanol, and the temperature at that time was 108° C. The results are shown in Table 1.

It can be seen from the gas-liquid equilibrium diagram shown in FIG. 2 that, in the azeotropic mixture of (2-methoxyethyl) vinyl ether and 2-methoxyethanol, removal of 2-methoxyethanol is difficult only by using two distillation columns and performing distillation under different pressure conditions since the change in azeotropic composition due to pressure is small.

TABLE 1

|  | Pressure | Temperature (° C.) | MEt content (% by mass) |
| --- | --- | --- | --- |
| Reference Example 1 | 60 kPa | 92 | 6.5 |
| Reference Example 2 | 26.7 kPa | 70 | 6.3 |
| Reference Example 3 | 40 kPa | 81 | 6.2 |
| Reference Example 4 | Atmospheric pressure | 108 | 9.0 |

MEt: 2-methoxyethanol

Reference Example 5: Gas-Liquid Equilibrium (Atmospheric Pressure) of Isooctane and 2-methoxyethanol The same operation as in Reference Example 1 was carried out except that the operation was carried out using 10 mL of 2-methoxyethanol and 150 mL of isooctane under atmospheric pressure.

The composition at the azeotropic point was 79.0% by mass of isooctane and 21.0% by mass of 2-methoxyethanol, and the temperature at that time was 92° C. The results are shown in Table 2.

Reference Example 6: Gas-Liquid Equilibrium (60 kPa) of Isooctane and 2-methoxyethanol The same operation as in Reference Example 1 was carried out except that 10 mL of 2-methoxyethanol and 150 mL of isooctane were used.

Figure 3:
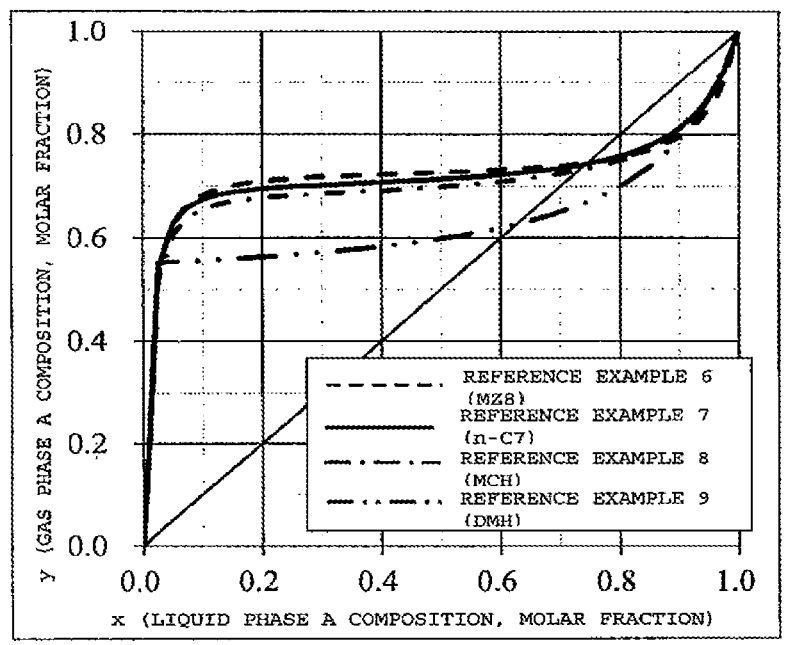
FIG. 3 is a graph showing gas-liquid equilibrium curves (XY diagrams) of mixtures of each of various azeotropic solvents and 2-methoxyethanol.

The gas-liquid equilibrium diagram of isooctane and 2-methoxyethanol at 60 kPa is shown in FIG. 3.

The composition at the azeotropic point was 81.5% by mass of isooctane and 18.5% by mass of 2-methoxyethanol, and the temperature at that time was 76° C. The results are shown in Table 2.

Reference Example 7: Gas-Liquid Equilibrium (60 kPa) of Normal Heptane and 2-methoxyethanol The same operation as in Reference Example 1 was carried out except that 10 mL of 2-methoxyethanol and 150 mL of normal heptane were used.

The gas-liquid equilibrium diagram of normal heptane and 2-methoxyethanol at 60 kPa is shown in FIG. 3.

The composition at the azeotropic point was 78.8% by mass of normal heptane and 21.2% by mass of 2-methoxyethanol, and the temperature at that time was 77° C. The results are shown in Table 2. Incidentally, known data are also listed as the azeotropic point and azeotropic composition under atmospheric pressure.

Reference Example 8: Gas-Liquid Equilibrium (60 kPa) of Methylcyclohexane and 2-methoxyethanol The same operation as in Reference Example 1 was carried out except that 10 mL of 2-methoxyethanol and 150 mL of methylcyclohexane were used.

The gas-liquid equilibrium diagram of methylcyclohexane and 2-methoxyethanol at 60 kPa is shown in FIG. 3.

The composition at the azeotropic point was 77.3% by mass of methylcyclohexane and 22.7% by mass of 2-methoxyethanol, and the temperature at that time was 78° C. The results are shown in Table 2. Incidentally, known data are also listed as the azeotropic point and azeotropic composition under atmospheric pressure.

Reference Example 9: Gas-Liquid Equilibrium (60 kPa) of 2,5-dimethylhexane and 2-methoxyethanol The same operation as in Reference Example 1 was carried out except that 10 mL of 2-methoxyethanol and 150 mL of 2,5-dimethylhexane were used.

The gas-liquid equilibrium diagram of 2,5-dimethylhexane and 2-methoxyethanol at 60 kPa is shown in FIG. 3.

The composition at the azeotropic point was 69.1% by mass of 2,5-dimethylhexane and 30.9% by mass of 2-methoxyethanol, and the temperature at that time was 84° C. The results are shown in Table 2. Incidentally, known data are also listed as the azeotropic point and azeotropic composition under atmospheric pressure.

TABLE 2

| | Solvent Component (A in FIGURE) | Pressure | Temperature (° C.) | MEt content (% by mass) |
|---|---|---|---|---|
| Reference Example 5 | MZ8 | Atmospheric pressure | 92 | 21.0 |
| Reference Example 6 | MZ8 | 60 kPa | 76 | 18.5 |
| Reference Example 7 | n-C7 | 60 kPa | 77 | 21.2 |
| | | Atmospheric pressure | 92.5 | 23.0 |
| Reference Example 8 | MCH | 60 kPa | 78 | 22.7 |
| | | Atmospheric pressure | 94 | 25.0 |
| Reference Example 9 | DMH | 60 kPa | 84 | 30.9 |
| | | Atmospheric pressure | 109 | 33.0 |

MEt: 2-methoxyethanol
MZ8: isooctane, n-C7: normal heptane, MCH: methylcyclohexane
DMH: 2,5-dimethylhexane It can be seen from the results shown in Table 2 and FIG. 3 that various solvents used in Reference Examples 5 to 9 form azeotrope with 2-methoxyethanol. Also, it can be seen that when isooctane, normal heptane and methylcyclohexane each having a normal boiling point of 92° C., 92.5° C. and 94° C. are used, it is easy to separate them from (2-methoxyethyl) vinyl ether having a normal boiling point of 108° C. In FIG. 3, MZ8 means isooctane, n-C7 means normal heptane, MCH means methylcyclohexane, and DMH means 2,5-dimethylhexane, respectively.

Example 1: Batch Distillation with Simulated Liquid

10 Parts by mass of 2-methoxyethanol and 90 parts by mass of (2-methoxyethyl) vinyl ether were mixed to prepare a simulated liquid of the crude vinyl ether. 1556 g of the simulated liquid and 622 g (about 4 times the amount of 2-methoxyethanol) of normal heptane as an azeotropic solvent were charged into a glass filling type precision distillation apparatus with an inner diameter of 50 mmφ and a theoretical plate number of 20 (filler: Laboratory packing of Sulzer Ltd), and subjected to batch distillation (azeotropic distillation) at a reflux ratio of 10, a final column top pressure of 60 kPa, and a heater temperature of 120° C. 2-Methoxyethanol and normal heptane were distilled from the top of the column at a column top temperature of 77° C. and a can liquid temperature of 85° C. The average azeotropic composition with a distillation ratio between 7 and 23% was 80.7% by mass of normal heptane, 18.9% by mass of 2-methoxyethanol and 0.4% by mass of (2-methoxyethyl) vinyl ether, and it found that (2-methoxyethyl) vinyl ether was hardly distilled. Further, it found that the distilled azeotropic mixture was separated into two layers at room temperature.

When the distillation ratio of each component of 2-methoxyethanol and normal heptane reached 95% or more, the reflux ratio was set to 1 and the heater temperature was set to 135° C., and (2-methoxyethyl) vinyl ether was distilled (rectification). (2-Methoxyethyl) vinyl ether was distilled at a column top temperature of 93° C. and a can liquid temperature of 94° C., and the purity of (2-methoxyethyl) vinyl ether reached a maximum of 99.4% (GC).

Figure 7:
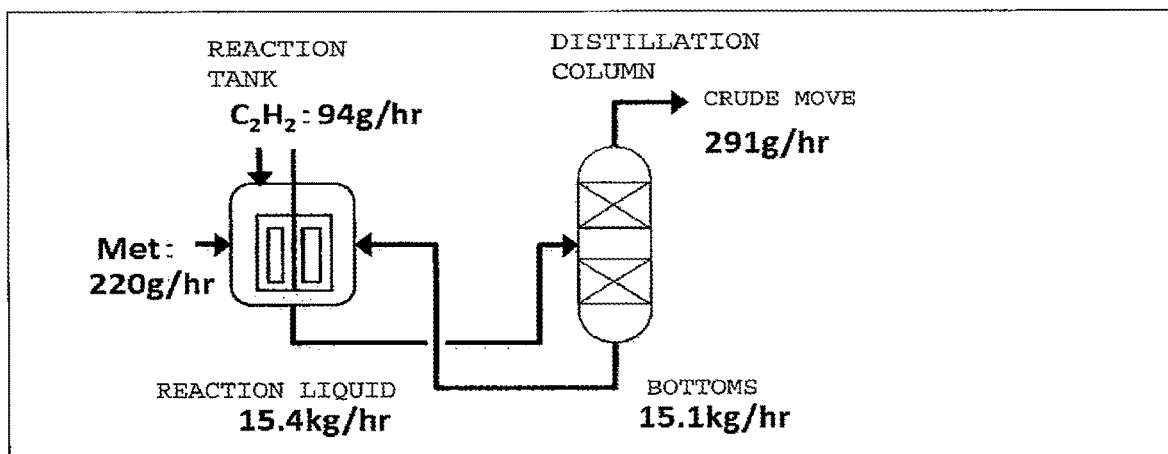
FIG. 7 is a diagram showing an apparatus used for preparation of a crude vinyl ether in Example 2.

Example 2: Batch Distillation (60 kPa) with Crude Vinyl Ether (1) The vinyl etherification step (addition reaction of alcohol to acetylene) and the catalyst removal step were performed using the apparatus shown in FIG. 7. A stainless steel autoclave with a capacity of 10 L as a reaction tank, and a stainless steel filling type continuous distillation column (filler: Sumitomo Heavy Industries, Ltd. Sumitomo/Sulzer Lab Packing) with an inner diameter of 60 mmφ, a theoretical plate number of 12 (7 feed plates), and a still volume of 4 L as a continuous distillation column in the latter stage were used, respectively. Specific procedures are shown below.

6.2 kg of 2-methoxyethanol (Met) and 1.4 kg of potassium hydroxide were charged into an autoclave, then the reaction conditions in the autoclave were set at 125° C., 0.03 MPaG and a residual oil amount to 5 L, and the conditions in the continuous distillation column were set at a top of the column of 70° C., a bottom of the column of 140° C., 20 kPa, a residual oil amount of 2 L and a reflux ratio of 5. At the same time, potassium-2-methoxyethan-1-olate was synthesized by operating at a circulation flow rate of 15 kg/hr between the autoclave and the continuous distillation column for 9 hours. During this period, the amount of distillate from the top of the continuous distillation column was 0.96 kg, and 0.38 kg of water was contained.

Next, the autoclave conditions were changed to 120° C. and 0.04 MPaG, and acetylene and 2-methoxyethanol were fed to the autoclave at a rate of 94 g/hr and at a rate of 220 g/hr, respectively.

Subsequently, the reaction liquid obtained by the above reaction was continuously fed to the continuous distillation column at a rate of 15.4 kg/hr. Here, the composition of the reaction liquid was as follows: 59.3% by mass of 2-methoxyethanol, 4.9% by mass of (2-methoxyethyl) vinyl ether, 34.0% by mass of potassium-2-methoxyethan-1-olate, and 1.7% by mass of heavy components.

Also, under the conditions of a reflux ratio of 5, a column top pressure of 40 kPa, a column top temperature of 80° C., and a can liquid temperature of 140° C., bottoms were extracted from the bottom of the continuous distillation column at 15.1 kg/hr, and fed to the autoclave. Here, the composition of the bottoms of the continuous distillation column was as follows: 60.3% by mass of 2-methoxyethanol, 3.2% by mass of (2-methoxyethyl) vinyl ether, 34.7% by mass of potassium-2-methoxyethan-1-olate, and 1.7% by mass of heavy components.

A crude vinyl ether was continuously synthesized as described above, and the crude vinyl ether was obtained at a flow rate of 291 g/hr from the top of the continuous distillation column. Here, the composition of the crude vinyl ether was 90.6% by mass of (2-methoxyethyl) vinyl ether and 9.4% by mass of 2-methoxyethanol.

(2) Batch distillation was carried out in the same manner as in Example 1, except that the simulated liquid of the crude vinyl ether was changed to 5270 g of the crude vinyl ether (containing 90.6% by mass of (2-methoxyethyl) vinyl ether and 9.4% by mass of 2-methoxyethanol, the same applies hereinafter), and the use amount of normal heptane was changed to 2450 g (about 5 times the amount of 2-methoxyethanol).

The average azeotropic composition under azeotropic distillation conditions was 80.4% by mass of normal heptane, 18.7% by mass of 2-methoxyethanol and 0.8% by mass of (2-methoxyethyl) vinyl ether, and it found that (2-methoxyethyl) vinyl ether was hardly distilled. Further, it found that the distilled azeotropic mixture was separated into two layers at room temperature.

Also, under rectification conditions, the purity of (2-methoxyethyl) vinyl ether reached a maximum of 99.8% (GC). In the rectification fraction with a (2-methoxyethyl) vinyl ether purity of 99% (GC), the concentration of 2-methoxy alcohol was 1.22% by mass and the concentration of normal heptane was 0.03% by mass.

Example 3: Batch Distillation (80 kPa) with Crude Vinyl Ether

Batch distillation was carried out in the same manner as in Example 1, except that 4740 g of the crude vinyl ether obtained in Example 2 (1) and 2210 g (about 5 times the amount of 2-methoxy alcohol) of normal heptane were poured into the residue of the still of Example 2 and the final column top pressure was changed to 80 kPa.

The azeotropic temperature (column top temperature) was 83° C., and the azeotropic composition was 79.8% by mass of normal heptane, 19.9% by mass of 2-methoxyethanol, and 0.3% by mass of (2-methoxyethyl) vinyl ether.

In the rectification fraction with a (2-methoxyethyl) vinyl ether purity of 99% (GC), the concentration of 2-methoxy alcohol was 0.81% by mass and the concentration of normal heptane was 0.16% by mass.

Example 4: Batch Distillation (Atmospheric Pressure) with Crude Vinyl Ether

Batch distillation was carried out in the same manner as in Example 1, except that 4200 g of the crude vinyl ether obtained in Example 2 (1) and 2000 g (about 5 times the amount of 2-methoxy alcohol) of normal heptane were poured into the residue of the still of Example 3 and the final column top pressure was changed to 102 kPa.

The azeotropic temperature (column top temperature) was 91° C., and the azeotropic composition was 78.1% by mass of normal heptane, 21.1% by mass of 2-methoxyethanol, and 0.5% by mass of (2-methoxyethyl) vinyl ether.

In the rectification fraction with a (2-methoxyethyl) vinyl ether purity of 99% (GC), the concentration of 2-methoxy alcohol was 0.72% by mass and the concentration of normal heptane was 0.19% by mass.

Example 5: Batch Distillation with Crude Vinyl Ether Using Isooctane as Azeotropic Solvent Batch distillation was carried out in the same manner as in Example 1, except that the simulated liquid of the crude vinyl ether was changed to 1800 g of the crude vinyl ether obtained in Example 2 (1) and the normal heptane was changed to 850 g (about 5 times the amount of 2-methoxyethanol) of isooctane.

The azeotropic temperature (column top temperature) was 76° C., and the azeotropic composition was 81.9% by mass of isooctane, 16.6% by mass of 2-methoxyethanol, and 1.4% by mass of (2-methoxyethyl) vinyl ether. Further, it found that the distilled azeotropic mixture was separated into two layers at room temperature.

Comparative Example 1: Batch Distillation with Crude Vinyl Ether Using Water as Azeotropic Solvent Batch distillation was carried out in the same manner as in Example 1, except that the simulated liquid of the crude vinyl ether was changed to 1800 g of the crude vinyl ether obtained in Example 2 (1), and the normal heptane was changed to 850 g (about 5 times the amount of 2-methoxyethanol) of water, the reflux ratio was changed to 1, and the final column top pressure was changed to 101.3 kPa.

The azeotropic temperature (column top temperature) was 84° C., and the azeotropic composition was 20.0% by mass of water, 0.1% by mass of 2-methoxyethanol, 79.5% by mass of (2-methoxyethyl) vinyl ether, and 0.4% by mass of acetaldehyde.

It found that 2-methoxyethanol was removed and the distilled azeotropic mixture was separated into two layers at room temperature. However, it can be seen that decomposition of the vinyl ether has occurred since acetaldehyde was detected. In addition, since separation of water that forms azeotrope with (2-methoxyethyl) vinyl ether is required in a later step, it is industrially disadvantageous to use water as the azeotropic solvent.

Reference Example 10: Liquid-Liquid Equilibrium Between Two Components of Normal Heptane and 2-methoxyethanol 8 g of normal heptane and 8 g of 2-methoxyethanol were added to a test tube, and the test tube was stoppered and stirred in a constant temperature oven (personal organic synthesizer ChemiStation PPS-25A manufactured by TOKYO RIKAKIKAI CO, LTD) under atmospheric pressure and nitrogen atmosphere at 0° C., 25° C. or 40° C. for 1.5 hours, and then allowed to stand for 4 hours or more.

Thereafter, when visually observed, it found that the above composition liquid was separated into two layers.

Both layers were collected with a syringe, and their compositions were analyzed respectively. The results are shown in Table 3.

Reference Example 11: Liquid-Liquid Equilibrium Between Three Components of Normal Heptane, 2-methoxyethanol and (2-methoxyethyl) Vinyl Ether (1)

The same operation as in Reference Example 10 was carried out except that 8 g of normal heptane, 8 g of 2-methoxyethanol and 0.16 g of (2-methoxyethyl) vinyl ether were added to a test tube and the test tube was stoppered. The results are shown in Table 3.

Reference Example 12: Liquid-Liquid Equilibrium Between Three Components of Normal Heptane, 2-methoxyethanol and (2-methoxyethyl) Vinyl Ether (2)

The same operation as in Reference Example 10 was carried out except that 8 g of normal heptane, 8 g of 2-methoxyethanol and 0.5 g of (2-methoxyethyl) vinyl ether were added to a test tube and the test tube was stoppered. The results are shown in Table 3.

Reference Example 13: Liquid-Liquid Equilibrium Between Three Components of Normal Heptane, 2-methoxyethanol and (2-methoxyethyl) Vinyl Ether (3)

The same operation as in Reference Example 10 was carried out except that 8 g of normal heptane, 8 g of 2-methoxyethanol and 1.0 g of (2-methoxyethyl) vinyl ether were added to a test tube and the test tube was stoppered, and the operation was carried out at a temperature of 0° C. or 25° C. The results are shown in Table 3.

Reference Example 14: Liquid-Liquid Equilibrium of Batch Distillation Azeotropic Composition Distillate The same operation as in Reference Example 10 was carried out except that 16 g of the azeotropic composition distillate obtained in Example 2 (80.4% by mass of normal heptane, 18.7% by mass of 2-methoxyethanol, 0.8% by mass of (2-methoxyethyl) vinyl ether) was added and the test tube was stoppered. The results are shown in Table 3.

Reference Example 15: Liquid-Liquid Equilibrium Between Two Components of Isooctane and 2-methoxyethanol The same operation as in Reference Example 10 was carried out except that 8 g of isooctane and 8 g of 2-methoxyethanol were added to the test tube and the test tube was stoppered. The results are shown in Table 3.

Reference Example 16: Liquid-Liquid Equilibrium Between Three Components of Isooctane, 2-methoxyethanol and (2-methoxyethyl) Vinyl Ether (1)

The same operation as in Reference Example 10 was carried out except that 8 g of isooctane, 8 g of 2-methoxyethanol and 0.16 g of (2-methoxyethyl) vinyl ether were added to the test tube and the test tube was stoppered. The results are shown in Table 3.

Reference Example 17: Liquid-Liquid Equilibrium Between Three Components of Isooctane, 2-methoxyethanol and (2-methoxyethyl) Vinyl Ether (2)

The same operation as in Reference Example 10 was carried out except that 8 g of isooctane, 8 g of 2-methoxyethanol and 0.5 g of (2-methoxyethyl) vinyl ether were added to the test tube and the tube was sealed. The results are shown in Table 3.

Reference Example 18: Liquid-Liquid Equilibrium Between Three Components of Isooctane, 2-methoxyethanol and (2-methoxyethyl) Vinyl Ether (3)

The same operation as in Reference Example 10 was carried out except that 8 g of isooctane, 8 g of 2-methoxyethanol and 1.0 g of (2-methoxyethyl) vinyl ether were added to a test tube and the test tube was stoppered, and the operation was carried out at a temperature of 0° C. or 25° C. The results are shown in Table 3.

Reference Example 19: Liquid-Liquid Equilibrium Between Two Components of Methylcyclohexane and 2-methoxyethanol The same operation as in Reference Example 10 was carried out except that 8 g of methylcyclohexane and 8 g of 2-methoxyethanol were added to a test tube and the test tube was stoppered, and the operation was carried out at a temperature of 20° C. The results are shown in Table 3.

Reference Example 20: Liquid-Liquid Equilibrium Between Three Components of Methylcyclohexane, 2-methoxyethanol and (2-methoxyethyl) Vinyl Ether The same operation as in Reference Example 10 was carried out except that 8 g of methylcyclohexane, 8 g of 2-methoxyethanol and 0.16 g of (2-methoxyethyl) vinyl ether were added to a test tube and the test tube was stoppered, and the operation was carried out at a temperature of 20° C. The results are shown in Table 3.

TABLE 3

| | | | Upper layer | | | Lower layer | | |
| --- | --- | --- | --- | --- | --- | --- | --- | --- |
| | Azeotropic solvent | Temperature (C. °) | MOVE (% by mass) | MEt (% by mass) | Azeotropic solvent (% by mass) | MOVE (% by mass) | MEt (% by mass) | Azeotropic solvent (% by mass) |
| Reference Example 10 | n-C7 | 0 | — | 3.6 | 96.4 | — | 91.5 | 8.5 |
| | | 25 | — | 10.2 | 89.8 | — | 84.7 | 15.3 |

TABLE 3-continued

|  | Azeotropic solvent | Temperature (C. °) | Upper layer | | | Lower layer | | |
|---|---|---|---|---|---|---|---|---|
|  |  |  | MOVE (% by mass) | MEt (% by mass) | Azeotropic solvent (% by mass) | MOVE (% by mass) | MEt (% by mass) | Azeotropic solvent (% by mass) |
|  |  | 40 | — | 18.9 | 81.1 | — | 78.1 | 21.9 |
| Reference Example 11 | n-C7 | 0 | 0.65 | 3.9 | 95.5 | 1.4 | 89.8 | 8.8 |
|  |  | 25 | 0.76 | 10.8 | 88.4 | 1.2 | 82.6 | 16.2 |
|  |  | 40 | 0.84 | 20.7 | 78.4 | 1.1 | 75.2 | 23.6 |
| Reference Example 12 | n-C7 | 0 | 2.0 | 4.3 | 93.7 | 4.4 | 86.1 | 9.5 |
|  |  | 25 | 2.5 | 13.0 | 84.5 | 3.8 | 78.1 | 18.0 |
|  |  | 40 | 2.9 | 27.0 | 70.1 | 3.5 | 66.9 | 29.6 |
| Reference Example 13 | n-C7 | 0 | 4.0 | 3.9 | 92.1 | 8.3 | 81.1 | 10.5 |
|  |  | 25 | 5.1 | 16.2 | 78.6 | 7.3 | 70.7 | 21.9 |
| Reference Example 14 | n-C7 | 0 | 0.40 | 3.7 | 95.9 | 0.91 | 90.5 | 8.6 |
|  |  | 25 | 0.46 | 10.5 | 89.0 | 0.75 | 83.6 | 15.7 |
|  |  | 40 | 0.48 | 17.6 | 81.9 | 0.68 | 79.1 | 20.2 |
| Reference Example 15 | MZ8 | 0 | — | 4.1 | 95.9 | — | 91.4 | 8.6 |
|  |  | 25 | — | 10.2 | 89.8 | — | 84.8 | 15.2 |
|  |  | 40 | — | 21.5 | 78.5 | — | 76.3 | 23.7 |
| Reference Example 16 | MZ8 | 0 | 0.66 | 4.3 | 95.0 | 1.4 | 89.7 | 8.9 |
|  |  | 25 | 0.81 | 11.5 | 87.7 | 1.3 | 82.8 | 15.9 |
|  |  | 40 | 0.88 | 18.9 | 80.2 | 1.2 | 73.5 | 25.2 |
| Reference Example 17 | MZ8 | 0 | 2.0 | 4.8 | 93.3 | 4.1 | 86.3 | 9.5 |
|  |  | 25 | 2.7 | 12.9 | 84.4 | 4.1 | 78.2 | 17.7 |
|  |  | 40 | 2.6 | 28.7 | 68.7 | 3.2 | 67.4 | 29.4 |
| Reference Example 18 | MZ8 | 0 | 3.3 | 5.2 | 91.6 | 6.6 | 83.2 | 10.2 |
|  |  | 25 | 4.0 | 13.8 | 82.2 | 5.9 | 75.3 | 18.7 |
| Reference Example 19 | MCH | 20 | — | 13.9 | 86.1 | — | 66.9 | 33.1 |
| Reference Example 20 | MCH | 20 | 0.88 | 22.1 | 77.0 | 1.2 | 61.4 | 37.5 |

MOVE: (2-methoxyethyl) vinyl ether,
MEt: 2-methoxyethanol
n-C7: normal heptane,
MZ8: isooctane,
MCH: methylcyclohexane From the results of Reference Examples 10 to 14, liquid-liquid equilibrium triangle diagrams of (2-methoxyethyl) vinyl ether, 2-methoxyethanol and normal heptane at each temperature were created. It is shown in FIG. 4.

From the results of Reference Examples 10 to 18, liquid-liquid equilibrium triangular diagrams of (2-methoxyethyl) vinyl ether, 2-methoxyethanol, and normal heptane or isooctane at 25° C. were created. It is shown in FIG. 5.

From the results of Reference Examples 19 and 20, a liquid-liquid equilibrium triangular diagram of (2-methoxyethyl) vinyl ether, 2-methoxyethanol and methylcyclohexane at 20° C. were created. It is shown in FIG. 5.

Figure 4:
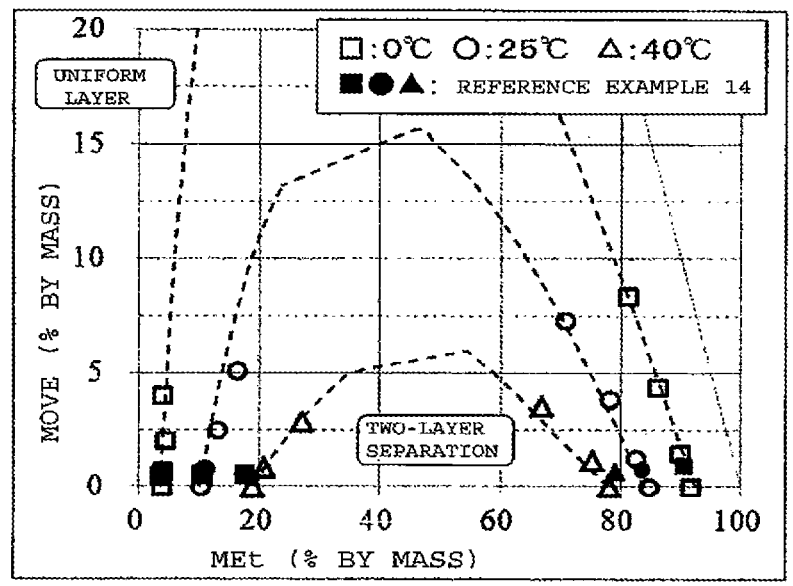
FIG. 4 is a graph showing liquid-liquid equilibrium diagrams of (2-methoxyethyl) vinyl ether, 2-methoxyethanol and normal heptane.
Figure 5:
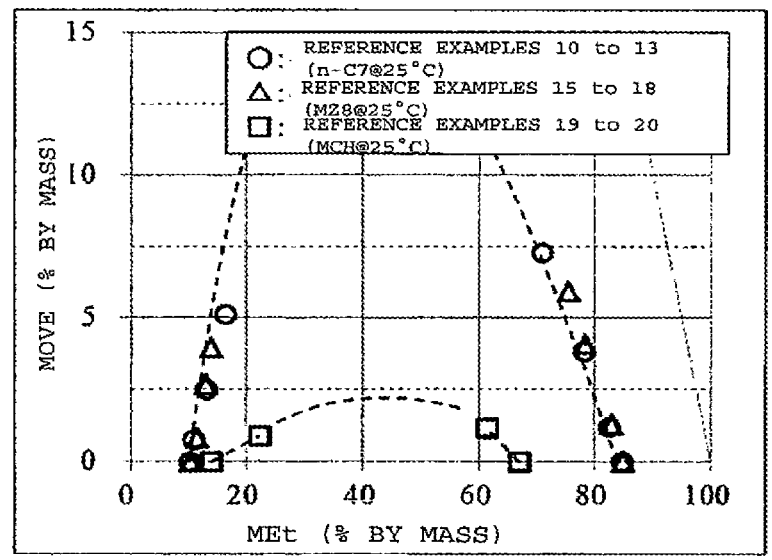
FIG. 5 is a graph showing liquid-liquid equilibrium diagrams of (2-methoxyethyl) vinyl ether, 2-methoxyethanol and each of various azeotropic solvents.

It found from FIG. 4 and FIG. 5 that any of the azeotropic solvents can be easily separated by two-phase separation. In particular, it found that when normal heptane or isooctane is used as the azeotropic solvent, the two-layer separation range is wide and they can be easily separated even without cooling to a low temperature.

Example 6: Continuous Azeotropic Distillation Simulation (Two-Layer Separation Tank: 30° C.)

In the embodiment shown in FIG. 1, a continuous azeotropic distillation simulation was performed under the following conditions.
Simulation software: PROII (manufactured by Invensys Process Systems)
Physical property estimation method: NRTL model
Apparatus: In the apparatus shown in FIG. 1, an apparatus equipped with the following was used.
As the azeotropic column 2, a distillation column of 52 theoretical plates (23 crude vinyl ether feed plates)
As the decanter 4, a two-layer separation tank
As the raw material recovery column 5, a distillation column of 3 theoretical plates (1 feed plate)
As the rectification column 7, a distillation column with a reflux ratio of 1 and 1 theoretical plate
In the azeotropic column 2, the raw material recovery column 5 and the rectification column 7, a reboiler is installed at the bottom of the column, and a condenser is installed at the top of the column As the crude vinyl ether 1, a mixed solution of 10% by mass of 2-methoxyethanol and 90% by mass of (2-methoxyethyl) vinyl ether was fed to the azeotropic column 2 at 112.3 kg/hr. As the azeotropic solvent 3, normal heptane was fed to the azeotropic column 2 at 0.8 kg/hr (1 feed plate). As the recovered raw material alcohol 6, solution containing 99% by mass of 2-methoxyethanol was extracted at 10.7 kg/hr. From the top of the raw material recovery column 5, a part of distillate was extracted at 0.3 kg/hr. As the product vinyl ether 8, a liquid containing 99% by mass of (2-methoxyethyl) vinyl ether was extracted at 100 kg/hr. From the bottom of the rectification column 7, bottoms were extracted at 2.0 kg/hr.

Then, the required reflux amount and required energy when the temperature of the two-layer separation tank (decanter 4) was set at 30° C. (load 0 MJ/hr) and the distillation column pressure was set at 40 kPa, 60 kPa, 80 kPa or atmospheric pressure were obtained by simulation. The results are shown in Table 4 and FIG. 6.
Required reflux amount: Amount (kg/hr) of liquid refluxed to the top of the azeotropic column 2
Required energy (reboiler): Value obtained by dividing the total required amount of heat of each distillation column reboiler by the extraction amount (100 kg/hr) of the product vinyl ether amount Required energy (condenser): Value obtained by dividing the total required amount of heat of each distillation column condenser by the extraction amount (100 kg/hr) of the product vinyl ether amount Required energy (total): Sum of absolute values of the required energy (reboiler) and the required energy (condenser)

Example 7: Continuous Azeotropic Distillation Simulation (Two-Layer Separation Tank: 20° C.)

Simulation was performed in the same manner as in Example 6 except that the temperature of the two-layer separation tank was changed to 20° C.

Figure 6:
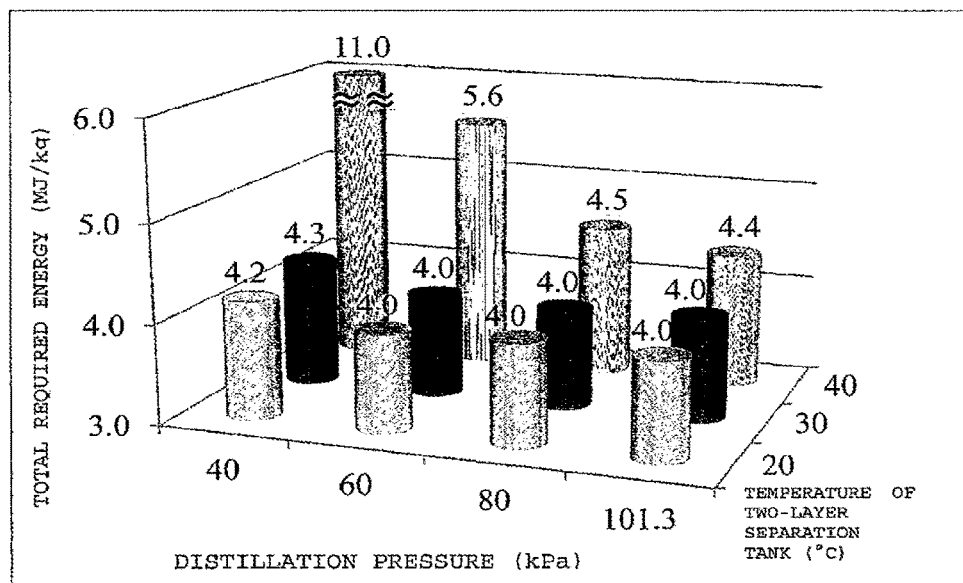
FIG. 6 is a graph showing the results of continuous azeotropic distillation simulation.

The results are shown in Table 4 and FIG. 6.

<Example 8: Continuous Azeotropic Distillation Simulation (Two-Layer Separation Tank: 40° C.)

Simulation was performed in the same manner as in Example 6 except that the temperature of the two-layer separation tank was changed to 40° C.

The results are shown in Table 4 and FIG. 6.

TABLE 4

| | Two-layer separation temperature (C. °) | Distillation pressure (kPa) | Required reflux amount (kg/hr) | Required energy | | |
|---|---|---|---|---|---|---|
| | | | | Reboiler (MJ/kg) | Condenser (MJ/kg) | Total (MJ/kg) |
| Example 6 | 30 | 40 | 283 | 2.2 | −2.1 | 4.3 |
| | | 60 | 244 | 2.1 | −1.9 | 4.0 |
| | | 80 | 233 | 2.1 | −1.9 | 4.0 |
| | | Atmospheric pressure | 231 | 2.1 | −1.9 | 4.0 |
| Example 7 | 20 | 40 | 266 | 2.2 | −2.0 | 4.2 |
| | | 60 | 233 | 2.1 | −1.9 | 4.0 |
| | | 80 | 230 | 2.1 | −1.9 | 4.0 |
| | | Atmospheric pressure | 220 | 2.1 | −1.9 | 4.0 |
| Example 8 | 40 | 40 | 1044 | 5.6 | −5.4 | 11.0 |
| | | 60 | 414 | 2.9 | −2.7 | 5.6 |
| | | 80 | 295 | 2.4 | −2.2 | 4.5 |
| | | Atmospheric pressure | 269 | 2.3 | −2.1 | 4.4 |

From Table 4 and FIG. 6, it found that energy efficiency can be improved by setting the distillation pressure to more than 40 kPa or setting the temperature of the two-layer separation tank to less than 40° C. In particular, it found that both the reboiler load and the condenser load can be suppressed by setting the combination of the distillation pressure and the temperature of the two-layer separation tank to a combination of a distillation pressure of more than 40 kPa and a temperature of the two-layer separating tank of less than 40° C., thereby energy efficiency can be greatly improved.

Example 9: Continuous Distillation of Azeotropic Column with Crude Vinyl Ether

Continuous distillation of azeotropic column was carried out using an apparatus equipped with a glass filling type distillation column (filler: Kiriyama PAC of Kiriyama Glass Works Co.) with an inner diameter of 25 mmφ and a theoretical plate number of 55 as the azeotropic column 2 in FIG. 1, and a jacketed Widmer type fractionation receiver as the decanter 4.

400 g of a crude vinyl ether consisting of 9.8% by mass of 2-methoxyethanol and 90.2% by mass of (2-methoxyethyl) vinyl ether and 100 g of normal heptane were charged into the azeotropic column 2, and a total reflux distillation was performed at a column top pressure of 60 kPa and a heater temperature of 140° C. for 2 hours. At this time, the inner temperature of the Widmer type fractionation receiver was kept at 30° C. by allowing cooling water to flow through the jacket.

Thereafter, a crude vinyl ether having the same composition as that charged into the azeotropic column 2 was fed as the crude vinyl ether 1 in FIG. 1 at 118 g/hr (25 feed plates), and normal heptane was fed as the azeotropic solvent 3 at 3.2 g/hr (1 feed plate), respectively. Further, the upper layer portion of the distillate in the Widmer type fractionation receiver was refluxed to the top of the azeotropic column at 241 g/hr, and the lower layer portion of the distillate was extracted at 15 g/hr. On the other hand, bottoms were extracted from the bottom of the azeotropic column at 106 g/hr, and the operation was continued for 15 hours as it was. At this time, the column top temperature was 76° C., and the can liquid temperature was 94° C. The composition of the upper layer portion of the distillate was 82.2% by mass of normal heptane, 13.9% by mass of 2-methoxyethanol, 4.1% by mass of (2-methoxyethyl) vinyl ether, the composition of the lower layer portion of the distillate was 18.7% by mass of normal heptane, 74.7% by mass of 2-methoxyethanol, 5.8% by mass of (2-methoxyethyl) vinyl ether and 0.6% by mass of water, and the composition of the bottoms was less than 0.01% by mass of normal heptane, 0.14% by mass of 2-methoxyethanol, and 99.7% by mass of (2-methoxyethyl) vinyl ether.

Also, the recovery rate of (2-methoxyethyl) vinyl ether was 99%.

From the results of Example 9, it found that, by azeotropic distillation using normal heptane as the azeotropic solvent, the 2-alkoxyethanol (1) can be easily and efficiently removed from the mixture containing the 2-alkoxyethanol (1) and the (2-alkoxyethyl) vinyl ether (2) forming an azeotropic composition while suppressing a decrease in the yield of (2-alkoxyethyl) vinyl ether (2), and high purity of (2-alkoxyethyl) vinyl ether (2) can be industrially advantageously produced.

Example 10: Batch Distillation of Raw Material Recovery Column with Azeotropic Column Distillate 404 g of the distillate obtained from the lower layer portion in the Widmer type fractionation receiver of Example 9 (18.7% by mass of normal heptane, 74.7% by mass of 2-methoxyethanol, 5.8% by mass of (2-methoxyethyl) vinyl ether, 0.6% by mass of water) was charged into a glass filling type distillation column (filler: Kiriyama PAC of Kiriyama Glass Works Co.) with an inner diameter of 25 mmφ and a theoretical plate number of 5, and subjected to batch distillation (raw material recovery) at a reflux ratio of 1, a final column top pressure of 60 kPa, and a heater temperature of 125° C.

108 g of distillate was distilled from the top of the column at a column top temperature of 107° C. and a can liquid temperature of 111° C. The composition of this distillate was 69.5% by mass of normal heptane, 14.0% by mass of 2-methoxyethanol, 13.6% by mass of (2-methoxyethyl) vinyl ether, and 2.2% by mass of water.

Further, 296 g of bottoms was obtained from the bottom of the column. The composition of the bottoms was less than 0.1% by mass of normal heptane, 97.0% by mass of 2-methoxyethanol, 2.9% by mass of (2-methoxyethyl) vinyl ether, and less than 0.1% by mass of water.

At this time, the recovery rate of 2-methoxyethanol was 95%.

It can be seen from the results of Example 10 that the 2-alkoxyethanol (1) can be easily and efficiently recovered from the 2-alkoxyethanol phase after liquid-liquid separation.

REFERENCE SIGNS LIST

1 Crude vinyl ether
2 Azeotropic column
3 Azeotropic solvent
4 Decanter
5 Raw material recovery column
6 Recovered raw material alcohol
7 Rectification column
8 Product vinyl ether

The invention claimed is:

1. A method for removing a 2-alkoxyethanol, the method comprising:
   adding at least one azeotropic solvent selected from the group consisting of normal heptane, isooctane, and a combination thereof to a mixture comprising the 2-alkoxyethanol of the following formula (1):

and
   a (2-alkoxyethyl) vinyl ether of the following formula (2):

subjecting the mixture to azeotropic distillation, thereby removing the 2-alkoxyethanol from the mixture, wherein R is an alkyl group having 1 to 4 carbon atoms.

2. A method for recovering a 2-alkoxyethanol, the method comprising:
   adding at least one azeotropic solvent selected from the group consisting of normal heptane, isooctane, and a combination thereof to a mixture comprising the 2-alkoxyethanol of the following formula (1):

and
   a (2-alkoxyethyl) vinyl ether of the following formula (2):

to subject the mixture to azeotropic distillation, thereby forming a distilled azeotropic mixture, and
   separating the distilled azeotropic mixture into an 2-alkoxyethanol phase and an azeotropic solvent phase by liquid-liquid separation, thereby recovering a 2-alkoxyethanol, wherein R is an alkyl group having 1 to 4 carbon atoms.

3. The method according to claim 1, wherein the mixture comprising the 2-alkoxyethanol and the (2-alkoxyethyl) vinyl ether is a reaction mixture obtained by a vinyl etherification reaction with the 2-alkoxyethanol as a raw material alcohol.

4. A method for producing a (2-alkoxyethyl) vinyl ether, the method comprising:
   conducting a vinyl etherification of a 2-alkoxyethanol of the following formula (1):

as a raw material alcohol, to obtain a reaction mixture comprising an unreacted raw material alcohol and the (2-alkoxyethyl) vinyl ether of the following formula (2):

and
   conducting azeotropic distillation by adding at least one azeotropic solvent selected from the group consisting of normal heptane, isooctane, and a combination thereof to the reaction mixture to remove the raw material alcohol, thereby producing a (2-alkoxyethyl) vinyl ether, wherein R is an alkyl group having 1 to 4 carbon atoms.

5. A method for producing a (2-alkoxyethyl) vinyl ether, the method comprising:
   conducting a vinyl etherification of a 2-alkoxyethanol of the following formula (1):

as a raw material alcohol, in the presence of a catalyst, to obtain a reaction mixture comprising an unreacted raw material alcohol and the (2-alkoxyethyl) vinyl ether of the following formula (2):

removing the catalyst from the reaction mixture, and
   conducting azeotropic distillation by adding at least one azeotropic solvent selected from the group consisting of normal heptane, isooctane, and a combination thereof to the reaction mixture after the catalyst removal to remove the raw material alcohol, thereby producing a (2-alkoxyethyl) vinyl ether, wherein R is an alkyl group having 1 to 4 carbon atoms.

6. The method according to claim 4, further comprising:
   separating a mixture distilled in the conducting azeotropic distillation into a raw material alcohol phase and an azeotropic solvent phase by liquid-liquid separation, and
   feeding at least a part of the azeotropic solvent phase to the conducting azeotropic distillation.

7. The method according to claim 6, further comprising:
feeding at least a part of the raw material alcohol phase to the conducting vinyl etherification.

8. The method according to claim 1, wherein R is a methyl group or an ethyl group.

9. The method according to claim 2, wherein the mixture comprising the 2-alkoxyethanol and the (2-alkoxyethyl) vinyl ether is a reaction mixture obtained by a vinyl etherification reaction with the 2-alkoxyethanol as a raw material alcohol.

10. The method according to claim 5, further comprising:
separating a mixture distilled in the conducting azeotropic distillation into a raw material alcohol phase and an azeotropic solvent phase by liquid-liquid separation, and
feeding at least a part of the azeotropic solvent phase to the conducting azeotropic distillation.

11. The method according to claim 10, further comprising:
feeding at least a part of the raw material alcohol phase to the conducting vinyl etherification.

12. The method according to claim 2, wherein R is a methyl group or an ethyl group.

13. The method according to claim 4, wherein R is a methyl group or an ethyl group.

14. The method according to claim 1, wherein an amount of the at least one azeotropic solvent is from 0.01 to 50 times by mass relative to the 2-alkoxyethanol.

15. The method according to claim 1, wherein an amount of the at least one azeotropic solvent is from 4 to 10 times by mass relative to the 2-alkoxyethanol.

16. The method according to claim 2, wherein an amount of the at least one azeotropic solvent is from 0.01 to 50 times by mass relative to the 2-alkoxyethanol.

17. The method according to claim 4, wherein an amount of the at least one azeotropic solvent is from 0.01 to 50 times by mass relative to the 2-alkoxyethanol.

18. The method according to claim 5, wherein an amount of the at least one azeotropic solvent is from 0.01 to 50 times by mass relative to the 2-alkoxyethanol.

* * * * *